United States Patent
Sarkar (10) Patent No.: US 9,675,270 B2
(45) Date of Patent: Jun. 13, 2017

(54) METHOD AND APPARATUS FOR DETERMINING A PREMATURE VENTRICULAR CONTRACTION IN A MEDICAL MONITORING DEVICE

(71) Applicant: Medtronic, Inc., Minneapolis, MN (US)

(72) Inventor: Shantanu Sarkar, Roseville, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 15/133,354

(22) Filed: Apr. 20, 2016

(65) Prior Publication Data

US 2016/0310031 A1    Oct. 27, 2016

Related U.S. Application Data (63) Continuation-in-part of application No. 14/694,847, filed on Apr. 23, 2015, now abandoned.

(51) Int. Cl.
| | | |
|---|---|---|
| *A61B 5/00* | (2006.01) | |
| *A61B 5/0468* | (2006.01) | |
| *A61B 5/0456* | (2006.01) | |
| *A61B 5/042* | (2006.01) | |
| *A61B 5/04* | (2006.01) | |

(52) U.S. Cl.
CPC ........ *A61B 5/0468* (2013.01); *A61B 5/04012* (2013.01); *A61B 5/0422* (2013.01); *A61B 5/0456* (2013.01); *A61B 5/686* (2013.01)

(58) Field of Classification Search
CPC . A61B 5/0468; A61B 5/04012; A61B 5/0422; A61B 5/0456; A61B 5/686
See application file for complete search history.

(56) References Cited

U.S. PATENT DOCUMENTS

| | | |
|---|---|---|
| 3,616,791 A | 11/1971 | Harris |
| 4,181,135 A | 1/1980 | Andresen et al. |
| 5,819,007 A | 10/1998 | Elghazzawi |
| 5,987,352 A | 11/1999 | Klein et al. |

(Continued)

FOREIGN PATENT DOCUMENTS

| | | |
|---|---|---|
| DE | 102006057882 A1 | 3/2008 |
| WO | 2007043903 A1 | 4/2007 |

OTHER PUBLICATIONS

Tsipouras et al, "An Arrhythmia Classification System Based on the RR-Interval Signal", Artificial Intelligence in Medicine, vol. 33, No. 3, Mar. 1, 2005, pp. 237-250.

(Continued)

*Primary Examiner* — Scott Getzow (57) ABSTRACT

A method and medical monitoring device for determining the occurrence of a premature ventricular contraction that includes sensing a cardiac signal and determining R-waves in response to the sensed cardiac signal, determining RR intervals between the determined R-waves, determining whether a first interval criteria is satisfied in response to the determined intervals, determining a correlation between the determined R-waves, determining whether a first correlation criteria is satisfied in response to the determined correlation, and determining the premature ventricular contraction is occurring in response to the first interval criteria and the first correlation criteria being satisfied.

31 Claims, 6 Drawing Sheets

(56) References Cited

U.S. PATENT DOCUMENTS

| | | |
|---|---|---|
| 6,393,316 B1 | 5/2002 | Gillberg et al. |
| 6,671,548 B1 | 12/2003 | Mouchawar et al. |
| 6,871,089 B2 | 3/2005 | Korzinov et al. |
| 6,954,671 B1 | 10/2005 | Hoijer et al. |
| 7,532,924 B2 | 5/2009 | Ternes |
| 7,751,876 B2 | 7/2010 | Healey |
| 7,783,349 B2 | 8/2010 | Libbus et al. |
| 7,869,870 B1 | 1/2011 | Farazi |
| 8,027,722 B1 | 9/2011 | Nabutovsky |
| 8,369,938 B2 | 2/2013 | Dong et al. |
| 8,457,728 B2 | 6/2013 | Schneider et al. |
| 8,600,489 B2 | 12/2013 | Warren et al. |
| 8,600,503 B1 | 12/2013 | Farazi |
| 8,744,559 B2 | 6/2014 | Houben et al. |
| 8,855,755 B2 | 10/2014 | Zhang et al. |
| 8,880,161 B2 | 11/2014 | Warren et al. |
| 2004/0015205 A1* | 1/2004 | Whitehurst ........ A61N 1/37205 607/48 |
| 2007/0255345 A1 | 11/2007 | Krause |
| 2008/0015651 A1 | 1/2008 | Ettori et al. |
| 2008/0140143 A1 | 6/2008 | Ettori et al. |
| 2009/0234409 A1 | 9/2009 | Shuros et al. |
| 2010/0004713 A1 | 1/2010 | Warren et al. |
| 2010/0249626 A1 | 9/2010 | El Arab et al. |
| 2011/0152957 A1 | 6/2011 | Shaquer |
| 2011/0184297 A1 | 7/2011 | Vitali et al. |
| 2012/0101541 A1 | 4/2012 | Corbucci et al. |
| 2012/0238891 A1 | 9/2012 | Sarkar et al. |
| 2013/0041273 A1 | 2/2013 | Houben et al. |
| 2013/0144180 A1 | 6/2013 | Chon et al. |
| 2014/0046396 A1 | 2/2014 | Warren et al. |
| 2015/0073246 A1 | 3/2015 | Chmiel et al. |
| 2016/0113537 A1 | 4/2016 | Cao et al. |

OTHER PUBLICATIONS

Tsipouras et al, "An Arrhythmia Classification System Based on the RR-Interval Signal", Computers in Cardiology 2002, vol. 29, Sep. 22-25, 2002, pp. 485-488.

(PCT/US2016/028428) PCT Notification of Transmittal of the International Search Report and the Written Opinion of the International Searching Authority, Mailed Jun. 28, 2016, 13 pages.

(U.S. Appl. No. 14/694,847), Office Action mailed Apr. 27, 2016, 16 pages.

* cited by examiner

METHOD AND APPARATUS FOR DETERMINING A PREMATURE VENTRICULAR CONTRACTION IN A MEDICAL MONITORING DEVICE

This application is a continuation-in-part of U.S. application Ser. No. 14/694,847 filed Apr. 23, 2015, the content of which is incorporated by reference in this application.

TECHNICAL FIELD

The disclosure relates generally to a medical monitoring device for monitoring a cardiac signal, and more particular, to a medical monitoring device for monitoring the occurrence of premature ventricular contractions in a cardiac signal to evaluate cardiac condition.

BACKGROUND

Numerous implantable medical devices are available for acute or chronic implantation within patients. Some implantable medical devices may be used to chronically monitor physiological signals of the patient, such as implantable hemodynamic monitors, implantable cardiac monitors (sometimes referred to as implantable loop recorders or ECG monitors), implantable blood chemistry monitors, implantable pressure monitors, or the like. Other implantable devices may be configured to deliver a therapy in conjunction with or separate from the monitoring of physiological signals.

Premature ventricular contractions (PVCs) may occur frequently in healthy individuals and may be caused by caffeine, smoking, alcohol consumption, stress, exhaustion, pharmacological toxicity, among other causes. An implantable monitoring device capable of detecting PVC burden may be a useful tool in some instances to evaluate cardiac wellness, perform risk stratification for sudden cardiac death or evaluate safety in pharmaceutical trials. Therefore, what is needed is an implantable monitoring device for monitoring occurrence of premature ventricular contractions to evaluate cardiac condition.

SUMMARY

According to one exemplary embodiment, a method includes sensing a cardiac signal and determining R-waves in response to the sensed cardiac signal, determining RR intervals between the determined R-waves, determining whether a first interval criteria is satisfied in response to the determined intervals, determining a correlation between the determined R-waves, determining whether a first correlation criteria is satisfied in response to the determined correlation and determining the premature ventricular contraction is occurring in response to the first interval criteria and the first correlation criteria being satisfied.

According to one exemplary embodiment, a medical monitoring device includes at least one sensing electrode for sensing a cardiac signal, and a processor configured to determine R-waves in response to the sensed cardiac signal, determine RR intervals between the determined R-waves, determine whether a first interval criteria is satisfied in response to the determined intervals, determine a correlation between the determined R-waves, determine whether a first correlation criteria is satisfied in response to the determined correlation, and determine the premature ventricular contraction is occurring in response to the first interval criteria and the first correlation criteria being satisfied.

According to one exemplary embodiment, an implantable cardiac monitoring device includes a proximal electrode located at a proximal end of the medical monitoring device and a distal electrode located at a distal end of the medical monitoring device for sensing cardiac signals. The implantable cardiac monitoring device includes electronic circuitry configured to detect or determine R-waves in response to the sensed cardiac signal, determine RR intervals between the determined R-waves, determine whether a first interval criteria is satisfied in response to the determined intervals, determine a correlation between the determined R-waves, determine whether a first correlation criteria is satisfied in response to the determined correlation, and determine the premature ventricular contraction is occurring in response to the first interval criteria and the first correlation criteria being satisfied.

DETAILED DESCRIPTION

Figure 1:
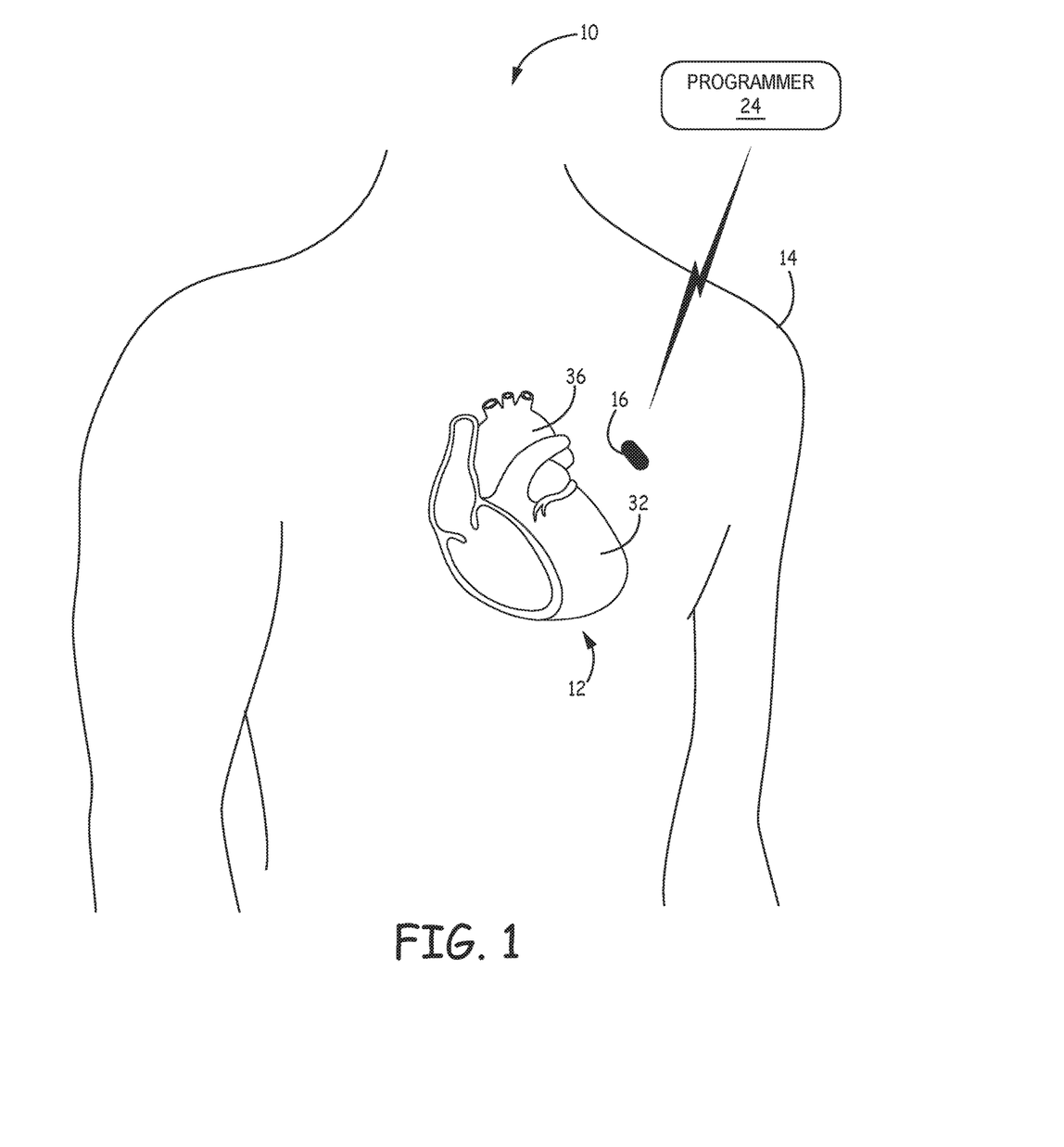
FIG. 1 is a conceptual diagram illustrating an exemplary implantable monitoring device system that may be used to monitor one or more physiological parameters of a patient according to the present disclosure.

FIG. 1 is a conceptual diagram illustrating an exemplary implantable monitoring device system that may be used to monitor one or more physiological parameters of a patient according to the present disclosure. As illustrated in FIG. 1, an implantable monitoring device system 10 includes a medical monitoring device or an implantable medical device (IMD) 16, which is coupled to programmer 24. IMD 16 may be a subcutaneous sensing device configured to sense signals indicative of one or more physiological parameters of patient 14. For example, IMD 16 may sense and/or store electrocardiogram (ECG) signals. In some examples, IMD 16 may be configured to sense ECG or other signals and detect arrhythmias, e.g., ventricular and/or supra-ventricular arrhythmias, based on the signals. An example of a monitoring device in the which the present disclosure may be utilized is described, for example, in U.S. Pat. No. 5,987,352 to Klein et al., incorporated herein by reference in its entirety. Another example of a monitoring device is a LINQ implantable cardiac monitor, available from Medtronic, Inc.

Although the examples described herein include IMD 16 configured to sense physiological signals of patient 14, in other examples IMD 16 may alternatively or additionally be configured to deliver therapy to patient 14. For example, IMD 16 may be an implantable leadless pacemaker that provides electrical signals to heart 12 via one or more electrodes (not shown in FIG. 1) on its outer housing, such as described, for example, in U.S. patent application Ser. No. 14/520,847, incorporated herein by reference in its entirety. Additionally or alternatively, IMD 16 may sense electrical signals attendant to the depolarization and repolarization of heart 12 via electrodes on its outer housing. In some examples, IMD 16 provides therapy to patient 14 based on sensed physiological signals.

In some examples, IMD 16 may be configured to be implanted proximate to heart 12, e.g., as illustrated in FIG. 1. In other examples, IMD 16 may be configured to be implanted proximate to or within another portion of the body of patient 14.

In the examples described herein, IMD 16 includes a header, which may include one or more components of IMD 16, and may be formed separately from the rest of IMD 16. In some examples, the header may include an antenna, at least one of the one or more electrodes, and/or an attachment plate configured to attach the header to another portion of IMD 16. The header may be formed via the molding techniques described herein.

In the example of FIG. 1, IMD 16 is positioned subcutaneously in a left pectoral region of patient 14. In other examples, however, IMD 16 may be positioned within any suitable region of patient 14. In some examples, depending on the location of implant, IMD 16 may include other sensing and/or stimulation functionalities. For example, IMD 16 may provide atrioventricular nodal stimulation, fat pad stimulation, vagal stimulation, or other types of neurostimulation, and/or may sense one or more parameters of heart 12 or another parameter of patient 12. In some examples, system 10 may include a plurality of leadless IMDs 16, e.g., to provide stimulation and/or sensing at a variety of locations.

FIG. 1 further depicts programmer 24 in communication with IMD 16. In some examples, programmer 24 comprises a handheld computing device, computer workstation, or networked computing device. Programmer 24 includes a user interface that presents information to and receives input from a user. It should be noted that the user may also interact with programmer 24 remotely via a networked computing device.

A user, such as a physician, technician, surgeon, electrophysiologist, other clinician, or patient, interacts with programmer 24 to communicate with IMD 16. For example, the user may interact with programmer 24 to retrieve physiological or diagnostic information from IMD 16. A user may also interact with programmer 24 to program IMD 16, e.g., select values for operational parameters of the IMD 16. For example, the user may use programmer 24 to retrieve information from IMD 16 regarding the rhythm of heart 12, trends therein over time, or arrhythmic episodes.

IMD 16 and programmer 24 may communicate via wireless communication using any techniques known in the art. Examples of communication techniques may include, for example, low frequency or radiofrequency (RF) telemetry, proximal inductive interaction, or tissue conductance communication, but other techniques are also contemplated. In some examples, programmer 24 may include a programming head that may be placed proximate to or in contact with the patient's body near the IMD 16 implant site in order to improve the quality or security of communication between IMD 16 and programmer 24.

Although the examples described herein refer to leadless IMD 16, IMD 16 may alternatively be coupled to one or more leads comprising one or more electrodes configured to sense the one or more physiological parameters of patient 14 and/or to deliver the therapy to heart 12 of patient 14. Additionally, although the examples herein describe monitoring physiological signals via IMD 16, IMD 16 may additionally or alternatively be configured for pacing therapy for heart 12, neurostimulation therapy, defibrillation therapy, or cardioversion therapy via one or more electrodes of system 10.

Figure 2:
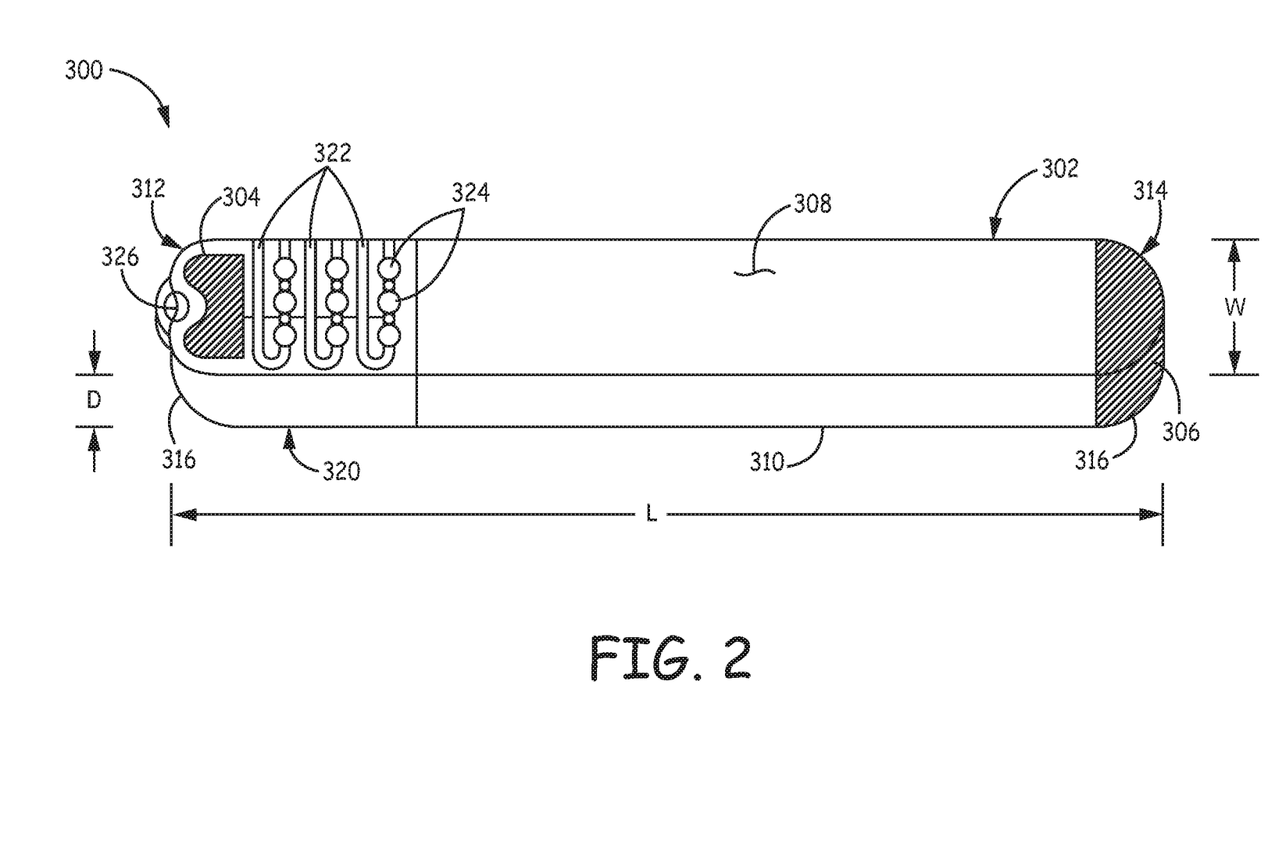
FIG. 2 is a schematic diagram of an exemplary insertable cardiac monitor for detecting a premature ventricular contraction according to the present disclosure.

FIG. 2 is a conceptual diagram of an example of an insertable cardiac monitor 300 for detecting or monitoring physiological parameters of a patient, e.g., a premature ventricular contraction, according to another embodiment of the present disclosure. In the embodiment shown in FIG. 2, insertable cardiac monitor 300 may be embodied as a monitoring device having housing 302, proximal electrode 304 and distal electrode 306. Housing 302 may further comprise first major surface 308, second major surface 310, proximal end 312, and distal end 314. Housing 302 encloses electronic circuitry 400 and power source 402 (shown in FIG. 3) located inside the insertable cardiac monitor 300 and protects the circuitry contained therein from body fluids. Electrical feedthroughs provide electrical connection of electrodes 304 and 306. Although not shown, electrical circuitry 400 may include any discrete and/or integrated electronic circuit components that implement analog and/or digital circuits capable of producing the functions described for analyzing EGM signals to detect/verify premature ventricular events. For example, the electrical circuitry 400 may include analog circuits, e.g., pre-amplification circuits, filtering circuits, and/or other analog signal conditioning circuits. The modules may also include digital circuits, e.g., digital filters, combinational or sequential logic circuits, state machines, integrated circuits, a processor (shared, dedicated, or group) that executes one or more software or firmware programs, memory devices, or any other suitable components or combination thereof that provide the described functionality.

In the embodiment shown in FIG. 2, insertable cardiac monitor 300 is defined by a length L, a width W and thickness or depth D and is in the form of an elongated rectangular prism wherein the length L is much larger than the width W, which in turn is larger than the depth D. In one embodiment, the geometry of the insertable cardiac monitor 300—in particular a width W greater than the depth D—is selected to allow the cardiac monitor 300 to be inserted under the skin of the patient using a minimally invasive procedure and to remain in the desired orientation during insert. For example, the device shown in FIG. 3 includes radial asymmetries (notably, the rectangular shape) along the longitudinal axis that maintains the device in the proper orientation following insertion. For example, in one embodiment the spacing between proximal electrode 304 and distal electrode 306 may range from 30 millimeters (mm) to 55 mm, 35 mm to 55 mm, and from 40 mm to 55 mm and may be any range or individual spacing from 25 mm to 60 mm. In addition, insertable cardiac monitor 300 may have a length L that ranges from 30 mm to about 70 mm. In other embodiments, the length L may range from 40 mm to 60 mm, 45 mm to 60 mm and may be any length or range of lengths between about 30 mm and about 70 mm. In addition, the width W of major surface 308 may range from 3 mm to 10 mm and may be any single or range of widths between 3 mm and 10 mm. The thickness of depth D of cardiac monitor device 300 may range from 2 mm to 9 mm. In other embodiments, the depth D of insertable cardiac monitor 300 may range from 2 mm to 5 mm and may be any single or range of depths from 2 mm to 9 mm. In addition, insertable cardiac monitor 300 according to an embodiment of the present invention is has a geometry and size designed for ease of implant and patient comfort. Embodiments of insertable cardiac monitor 300 described in this disclosure may have a volume of three cubic centimeters (cm) or less, 1.5 cubic cm or less or any volume between three and 1.5 cubic centimeters.

In the embodiment shown in FIG. 2, once inserted within the patient, the first major surface 308 faces outward, toward the skin of the patient while the second major surface 310 is located opposite the first major surface 308. In addition, in the embodiment shown in FIG. 2, proximal end 312 and distal end 314 are rounded to reduce discomfort and irritation to surrounding tissue once inserted under the skin of the patient. Insertable cardiac monitor 300, including instrument and method for inserting monitor 300 is described, for example, in U.S. Patent Publication No. 2014/0276928, incorporated herein by reference in its entirety.

As described with other embodiments, proximal electrode 304 and distal electrode 306 are used to sense cardiac signals for detecting a premature ventricular contraction, described below, e.g. ECG signals, intra-thoracically or extra-thoracically, which may be sub-muscularly or subcutaneously. ECG signals may be stored in a memory of the insertable cardiac monitor 300, and ECG data may be transmitted via integrated antenna 322 to another medical device, which may be another implantable device or an external device. In alternative applications, electrodes 304 and 306 may be used for sensing any bio-potential signal of interest, which may be, for example, an EGM, EEG, EMG, bio-impedance or a nerve signal, from any implanted location.

In the embodiment shown in FIG. 2, proximal electrode 304 is in close proximity to the proximal end 312 and distal electrode 306 is in close proximity to distal end 314. In this embodiment, distal electrode 306 is not limited to a flattened, outward facing surface, but may extend from first major surface 308 around rounded edges 316 and/or end surface 318 and onto the second major surface 310 so that the electrode 306 has a three-dimensional curved configuration. In the embodiment shown in FIG. 2, proximal electrode 304 is located on first major surface 308 and is substantially flat, outward facing. However, in other embodiments proximal electrode 304 may utilize the three dimensional curved configuration of distal electrode 306, providing a three dimensional proximal electrode (not shown in this embodiment). Similarly, in other embodiments distal electrode 306 may utilize a substantially flat, outward facing electrode located on first major surface 308 similar to that shown with respect to proximal electrode 304. The various electrode configurations allow for configurations in which proximal electrode 304 and distal electrode 306 are located on both first major surface 308 and second major surface 310. In other configurations, such as that shown in FIG. 2, only one of proximal electrode 304 and distal electrode 306 is located on both major surfaces 308 and 310, and in still other configurations both proximal electrode 304 and distal electrode 306 are located on one of the first major surface 308 or the second major surface 310 (i.e., proximal electrode 304 located on first major surface 308 while distal electrode 306 is located on second major surface 310). In another embodiment, cardiac monitor device 300 may include electrodes on both major surface 308 and 310 at or near the proximal and distal ends of the device, such that a total of four electrodes are included on cardiac monitor device 300. Electrodes 304 and 306 may be formed of a plurality of different types of biocompatible conductive material, e.g. stainless steel, titanium, platinum, iridium, or alloys thereof, and may utilize one or more coatings such as titanium nitride or fractal titanium nitride.

In the embodiment shown in FIG. 2, proximal end 312 includes a header assembly 320 that includes one or more of proximal electrode 304, integrated antenna 322, anti-migration projections 324, and/or suture hole 326. Integrated antenna 322 is located on the same major surface (i.e., first major surface 308) as proximal electrode 304 and is also included as part of header assembly 320. Integrated antenna 322 allows insertable cardiac monitor 300 to transmit and/or receive data. In other embodiments, integrated antenna 322 may be formed on the opposite major surface as proximal electrode 304, or may be incorporated within the housing 322 of insertable cardiac monitor 300. In the embodiment shown in FIG. 3, anti-migration projections 324 are located adjacent to integrated antenna 322 and protrude away from first major surface 308 to prevent longitudinal movement of the device. In the embodiment shown in FIG. 2, anti-migration projections 324 includes a plurality (e.g., nine) small bumps or protrusions extending away from first major surface 308. As discussed above, in other embodiments anti-migration projections 324 may be located on the opposite major surface as proximal electrode 304 and/or integrated antenna 322. In addition, in the embodiment shown in FIG. 2 header assembly 320 includes suture hole 326, which provides another means of securing insertable cardiac monitor 300 to the patient to prevent movement following insert. In the embodiment shown, suture hole 326 is located adjacent to proximal electrode 304. In one embodiment, header assembly 320 is a molded header assembly made from a polymeric or plastic material, which may be integrated or separable from the main portion of insertable cardiac monitor 300.

Figure 3:
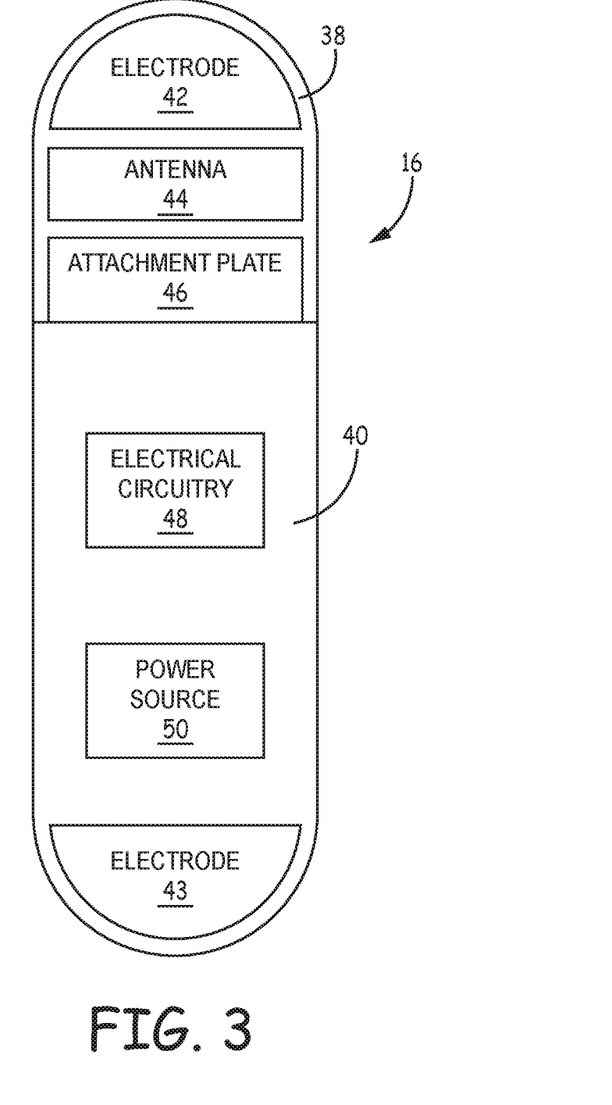
FIG. 3 is a functional block diagram of an exemplary implantable monitoring device that may be used to monitor one or more physiological parameters of a patient according to the present disclosure.

FIG. 3 is a functional block diagram of an exemplary implantable monitoring device, for example, the insertable cardiac monitor 300 as shown in FIG. 2, that may be used to monitor one or more physiological parameters of a patient according to the present disclosure. Accordingly, all of the dimensions and physical characteristics described above for the embodiment of FIG. 2 also apply and can be applied to the embodiment shown in FIG. 3. As illustrated in FIG. 3, IMD 16 may include header 38 coupled to body portion 40. In the examples described herein, header 38 may include proximal electrode 42, distal electrode 43, antenna 44, and attachment plate 46. In particular, proximal electrode 42, antenna 44, and attachment plate 46 may be molded into header 38 via a two-shot molding process. Body portion 40 of IMD 16 may include electrical circuitry 48 and power source 50, in some examples, which may be contained within a hermetic housing or can, e.g., formed of titanium or ceramic. Electrical circuitry 48 is coupled to proximal electrode 42 and distal electrode 43 to sense cardiac signals and monitor events, including detecting premature ventricular contractions as described in more detail below. Electrical circuitry 48 is also connected to transmit and receive communications via antenna 44. Power source 50 provides power to electrical circuitry 48, as well as to any other components that require power. Power source 50 may include one or more energy storage devices, such as one or more rechargeable or non-rechargeable batteries.

In the embodiment shown in FIG. 3, electrical circuitry 48 receives raw EGM signals monitored by proximal electrode 42 and distal electrode 43. Electrical circuitry 48 includes components/modules for converting the raw EGM signal to a processed EGM signal that can be analyzed to detect sense events. Although not shown, electrical circuitry 48 may include any discrete and/or integrated electronic circuit components that implement analog and/or digital circuits capable of producing the functions described for analyzing EGM signals to detect/verify bradycardia and/or asystole events. For example, the electrical circuitry 48 may include analog circuits, e.g., pre-amplification circuits, filtering circuits, and/or other analog signal conditioning circuits. The modules may also include digital circuits, e.g., digital filters, combinational or sequential logic circuits, state machines, integrated circuits, a processor (shared, dedicated, or group) that executes one or more software or firmware programs, memory devices, or any other suitable components or combination thereof that provide the described functionality.

As shown in FIG. 3, header 38 includes at least one proximal electrode 42 and one distal electrode 43 located at proximal 45 and distal 47 ends of the IMD, respectively. Proximal electrode 42 may be configured to sense physiological signals of patient 14 and/or to deliver electrical stimulation therapy to patient 14, e.g., to treat a cardiac disorder of patient 14. IMD 16 may sense signals or deliver stimulation via proximal electrode 42 in combination with another electrode, such as distal electrode 43 or the housing of body portion 40. In some examples, proximal electrode 42 and distal electrode 43 may be coated with a material configured to improve performance, e.g., sensing or pacing performance. As described above in the description of FIG. 2, electrodes 42, 43 may be coated with a conductive material such as Titanium Nitride (TiN).

Header 38 also includes antenna 44. Antenna 44 may be configured to transmit and/or receive electromagnetic signals for communication. For example, antenna 44 may be configured to transmit to and/or receive signals from programmer 24 via inductive coupling, electromagnetic coupling, tissue conductance, Near Field Communication (NFC), Radio Frequency Identification (RFID), BLUETOOTH®, WiFi, or other proprietary or non-proprietary wireless telemetry communication schemes. Antenna 44 may be coupled to electrical circuitry 48 of IMD 16, which may drive antenna 44 to transmit signals to programmer 24, and may receive signals received from programmer 24 via antenna 44. In the example shown in FIG. 3, header 38 additionally includes attachment plate 46, which is configured to mechanically couple header 38 to body portion 40 of IMD 16.

In the example shown in FIG. 3, body portion 40 of IMD 16 is configured to house electrical circuitry 48 and power source 50. Electrical circuitry 48 may comprise one or more electrical circuits configured to perform any function of IMD 16. For example, the electrical circuitry 48 may be coupled to antenna 44 to receive and/or transmit signals. Electrical circuitry 48 may additionally or alternatively be configured to analyze physiological signals, e.g., signals sensed via electrodes 42, 43, and/or to control delivery of stimulation or other therapies. Body portion 40 is also configured to house power source 50, which may be configured to provide energy to various components of IMD 16, such as electrical circuitry 48.

Figure 4:
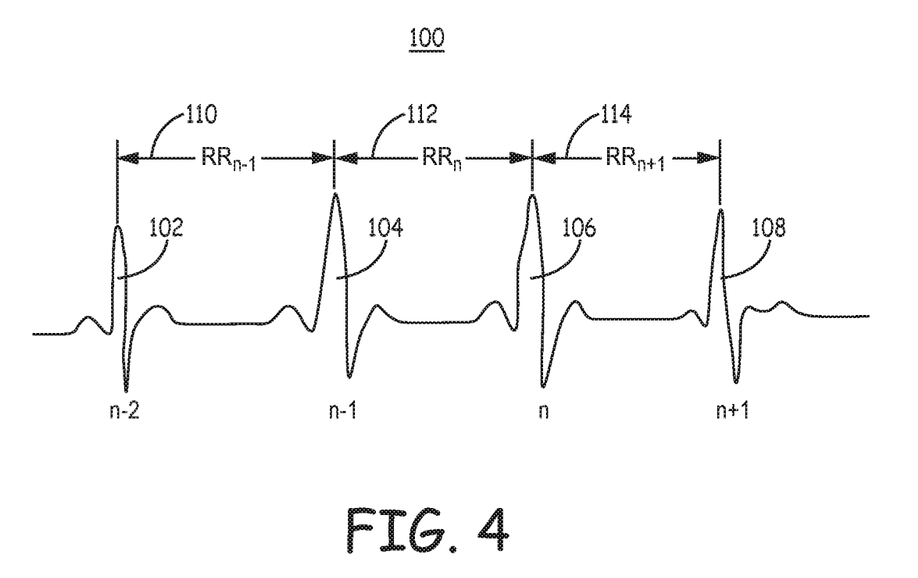
FIG. 4 is a schematic diagram illustrating detecting a premature ventricular contraction according to an embodiment of the present disclosure.

FIG. 4 is a schematic diagram illustrating detecting a premature ventricular contraction according to an embodiment of the present disclosure. As illustrated in FIG. 4, a cardiac signal 100 may be sensed by a monitoring device, such as a subcutaneous monitoring device, for example shown in FIGS. 2 and 3, from which the device identifies R-waves 102-108. In order to determine whether one of the R-waves 104-106 is associated with the occurrence of a premature ventricular contraction, the device determines interval differences between intervals formed by the detected R-waves 104-108 and a morphology criterion between the R-waves 104-108. For example, the device determines an RR interval 110 associated with the first detected R-wave 104 and a previously detected R-wave 102, an interval 112 associated with the second detected R-wave 106 and the previously detected R-wave 104, and an interval 114 associated with the third R-wave 108 and the previously detected R-wave 106. A premature ventricular contraction is then identified by comparing the differences between the RR intervals 110-114, as described below.

In addition to determining the interval differences to identify a premature ventricular contraction, the device also determines a morphology criterion that is used in combination with the interval differences to ascertain whether one of the intervals 104-108 is the result of a premature ventricular contraction being sensed. For example, the device determines a correlation between the morphology of the first R-wave 104 and the second R-wave 106, between the first R-wave 104 and the third R-wave 108, and between the second R-wave 106 and the third R-wave, using known correlation determination techniques. For example, a difference-sum technique may be utilized in which instead of multiplying, the baseline, which can be computed as the median of the waveform from first R-wave to last R-wave under consideration, is subtracted from the two waveforms, and a point by point difference is determined, and a sum of the difference is used to determine the correlation or match between the two waveforms. Two highly correlated waveforms will lead to a lower difference sum compared to two waveforms that are not highly correlated. According to another embodiment, wavelet based template matching is used to determine a correlation between the R-waves 104-108, such as described for example in U.S. Pat. No. 6,393,316 to Gillberg et al., incorporated herein by reference in it's entirety. During wavelet based template matching, two segments of waveforms, the template and the current beat are matched (same as cross-correlated) with each other using wavelet coefficients at three different lags, with the best match representing the match score (or cross-correlation).

According to another embodiment, a filter technique made be utilized to determine the correlation between the R-waves 104-108 in which one of the waveforms is used as filter coefficients of a digital FIR filter, and then the other waveform filtered using the first waveform as filter coefficients with the maximum output after the filtering being the best match (or cross-correlation) value. In yet another exemplary embodiment, a feature set matching technique may be utilized to determine correlation of the R-waves 104-108 in which rather than multiplying each point of the waveform, features are decoded from each waveform, such as amplitude maximum, amplitude minimum, amplitude mean and median, number of samples within a percentage of median, polarity (based on difference of max or min from mean value), r-wave width, r-wave area under curve. The feature set is then compared between the two waveforms to generate a match score, or correlation. It is understood that any known method for determining a correlation between R-waves may be utilized in order to carry out the determination of the occurrence of a premature ventricular contraction according to the present disclosure.

Figure 5:
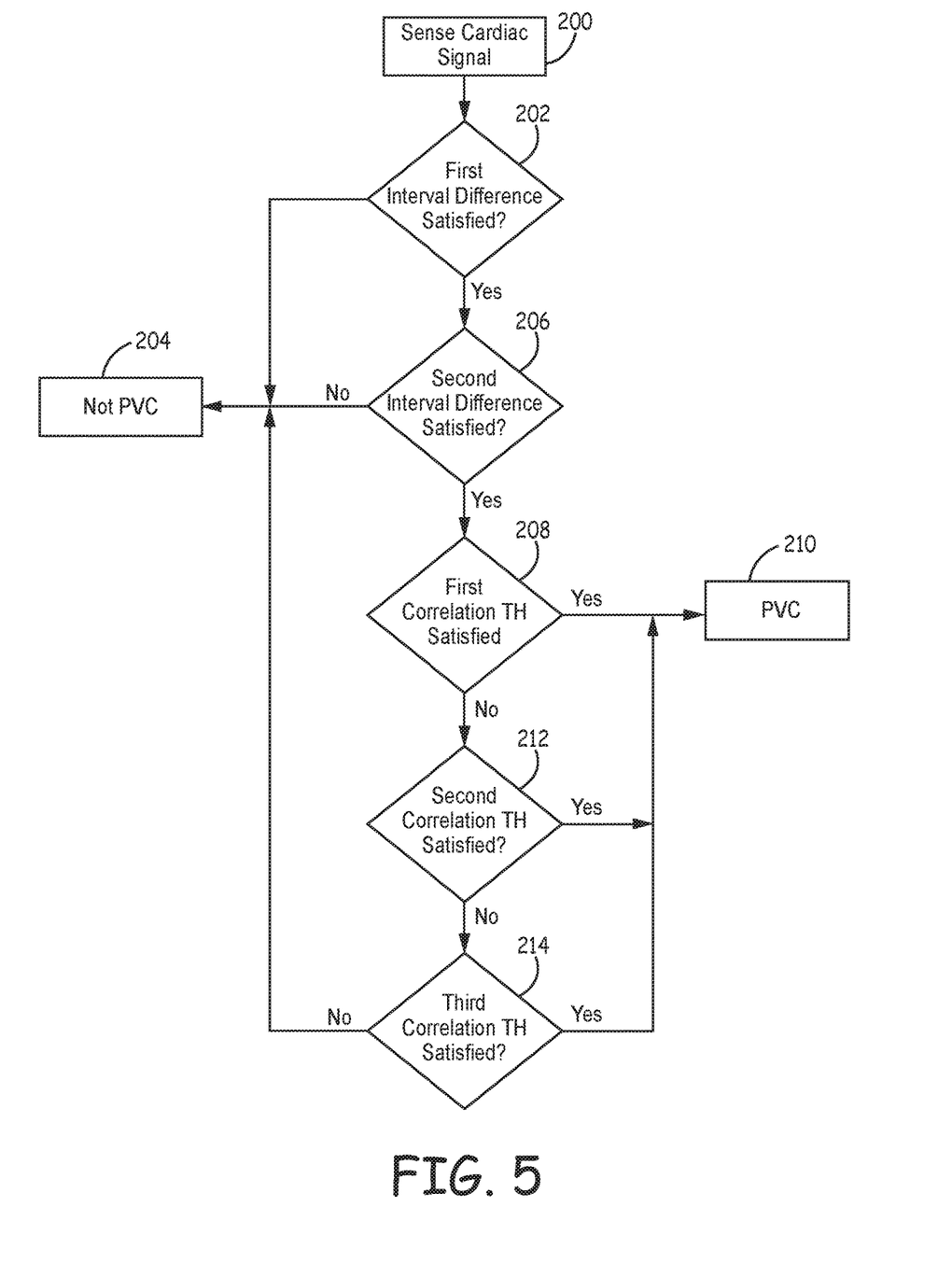
FIG. 5 is a flowchart of a method for detecting a premature ventricular contraction in a medical monitoring device according to an embodiment of the disclosure.

FIG. 5 is a flowchart of a method for detecting a premature ventricular contraction in a medical monitoring device according to an embodiment of the disclosure. As illustrated in FIGS. 4 and 5, the device senses the cardiac signal 100, Block 200, and determines R-waves 102-108 associated with the signal 100. The device determines whether a first interval difference associated with the R-waves is satisfied, Block 202, as described below. If the first interval difference is not satisfied, No in Block 202, a premature ventricular contraction is determined not to occur, Block 204. If the first interval difference threshold is satisfied, Yes in Block 202, the device determines whether a second interval difference is satisfied, Block 206. If the second interval difference is not satisfied, No in Block 206, a premature ventricular contraction is determined not to occur, Block 204. If the second interval difference is satisfied, Yes in Block 206, the device determines whether a first correlation threshold between the R-waves 104-108 is satisfied, Block 208.

If the first correlation threshold is satisfied, Yes in Block 208, a premature ventricular contraction is determined to have occurred, Block 210. If the first correlation threshold is not satisfied, No in Block 208, the device determines whether a second correlation threshold is satisfied, Block 212, described below. If the second correlation threshold is satisfied, Yes in Block 212, a premature ventricular contraction is determined to have occurred, Block 210. If the second correlation threshold is not satisfied, No in Block 212, the device determines whether a third correlation threshold is satisfied, Block 214, described below. If the third correlation threshold is satisfied, Yes in Block 214, a premature ventricular contraction is determined to have occurred, Block 210. If the third correlation threshold is not satisfied, No in Block 214, the device determines a premature ventricular contraction is determined not to occur, Block 204.

In this way, the device combines RR interval criteria with morphologic criteria to determine the presence of a ventricular contraction by determining the premature ventricular contraction when both the first and second interval difference thresholds are satisfied, Yes in Blocks 202 and 206, and at least one of the first, second or third correlation thresholds have been satisfied, Yes in Block 208, 212 or 214.

According to an embodiment of the disclosure, in order to determine whether the first interval difference is satisfied, the device compares the RR-interval 112 associated with the second R-wave 106 ($RR_n$) with both the RR-interval 104 associated with the first R-wave 104 ($RR_{n-1}$) and the RR-interval 114 associated with the third R-wave 108 ($RR_{n+i}$). A determination is made as to whether the RR-interval 112 associated with the second R-wave 106 ($RR_n$) is shorter than the RR-interval 104 associated with the first R-wave 104 ($RR_{n-1}$) with the difference being greater than an interval threshold, such as being greater than 10 ms, for example. If the difference is determined to be greater than the difference threshold, the first interval difference is determined to be satisfied, Yes in Block 202.

Similarly, a determination is made as to whether the RR-interval 112 associated with the second R-wave 106 ($RR_n$) is shorter than the RR-interval 114 associated with the third R-wave 104 ($RR_{n+1}$) with the difference being greater than an interval threshold, such as being greater than 10 ms, for example. If the difference is determined to be greater than the difference threshold, the second interval difference is determined to be satisfied, Yes in Block 206.

According to an embodiment of the disclosure, in order to determine whether the correlation thresholds 208-212 are satisfied, the device determines correlations between the R-waves 104-108 using known correlation schemes. In order to determine whether the first correlation threshold is satisfied, Block 208, a determination is made as to whether a first correlation ($C_{n-1,n+1}$) between the first R-wave 104 and the third R-wave 108 is greater than a correlation threshold, such as 0.9 for example. In addition, the device determines whether a difference between the first correlation and a second correlation ($C_{n-1,n}$) determined between the first R-wave 104 and the second R-wave 106 is greater than a correlation difference threshold, such as 0.1 for example, and whether a difference between the first correlation and a third correlation ($C_{n,n+1}$) between the second R-wave 106 and the third R-wave is greater than the correlation difference threshold. If the first correlation between the first R-wave 104 and the third R-wave 108 is greater than the correlation threshold, and both the difference between the first correlation and the second correlation and the difference between the first correlation and the third correlation is greater than the correlation difference threshold, the first correlation threshold is determined to be satisfied, Yes in Block 208.

According to an embodiment of the disclosure, in order to determine whether the second correlation threshold is satisfied, Block 212, a determination is made as to whether a first correlation ($C_{n-1,n+1}$) between the first R-wave 104 and the third R-wave 108 is greater than a correlation threshold, such as 0.8 for example. In addition, the device determines whether a difference between the first correlation and a second correlation ($C_{n-1,n}$) determined between the first R-wave 104 and the second R-wave 106 is greater than a correlation difference threshold, such as 0.3 for example, and whether a difference between the first correlation and a third correlation between the second R-wave 106 and the third R-wave is greater than the correlation difference threshold. If the first correlation between the first R-wave 104 and the third R-wave 108 is greater than the correlation threshold, and both the difference between the first correlation and the second correlation and the difference between the first correlation and the third correlation is greater than the correlation difference threshold, the second correlation threshold is determined to be satisfied, Yes in Block 212.

Similarly, in order to determine whether the third correlation threshold is satisfied, Block 214, a determination is made as to whether a first correlation ($C_{n-1,n+1}$) between the first R-wave 104 and the third R-wave 108 is greater than a correlation threshold, such as 0.7 for example. In addition, the device determines whether a difference between the first correlation and a second correlation ($C_{n-1,n}$) determined between the first R-wave 104 and the second R-wave 106 is greater than a correlation difference threshold, such as 0.6 for example, and whether a difference between the first correlation and a third correlation ($C_{n,n+1}$) between the second R-wave 106 and the third R-wave is greater than the correlation difference threshold. If the first correlation between the first R-wave 104 and the third R-wave 108 is greater than the correlation threshold, and both the difference between the first correlation and the second correlation and the difference between the first correlation and the third correlation is greater than the correlation difference threshold, the third correlation threshold is determined to be satisfied, Yes in Block 214.

In this way, the device determines the RR-interval criteria by evaluating the three RR-intervals 110-114 using the following evaluation criteria:

Criteria 1: $RR_n < RR_{n-1} - 10$ ms and $RR_n < RR_{n+1} - 10$ ms where $RR_n$ is the RR-interval 112 associated with the second R-wave 106, $RR_{n-1}$ is the RR-interval 110 associated with the first R-wave 104, and $RR_{n+1}$ is the RR-interval 114 associated with the third R-wave 108. In addition, the device determines the correlation criteria by evaluating the correlation of the three R-waves 104-108 using the following correlation criteria:

Criteria 2: $\{C_{n-1,n+1} > 0.9$ and $C_{n-1,n+1} - C_{n-1,n} > 0.1$ and $C_{n-1,n+1} - C_{n,n+1} > 0.1\}$ OR $\{C_{n-1,n+1} > 0.8$ and $C_{n-1,n+1} - C_{n-1,n} > 0.3$ and $C_{n-1,n+1} - C_{n,n+1} > 0.3\}$ OR $\{C_{n-1,n+1} > 0.7$ and $C_{n-1,n+1} - C_{n-1,n} > 0.6$ and $C_{n-1,n+1} - C_{n,n+1} > 0.6\}$ where $C_{n-1,n+1}$ is the cross-correlation between the first R-wave 104 and the third R-wave 108, $C_{n-1,n}$ is the cross correlation between first R-wave 104 and the second R-wave 106, $C_{n,n-1}$ is the cross correlation between the second R-wave 106 and the third R-wave 108.

Figure 6:
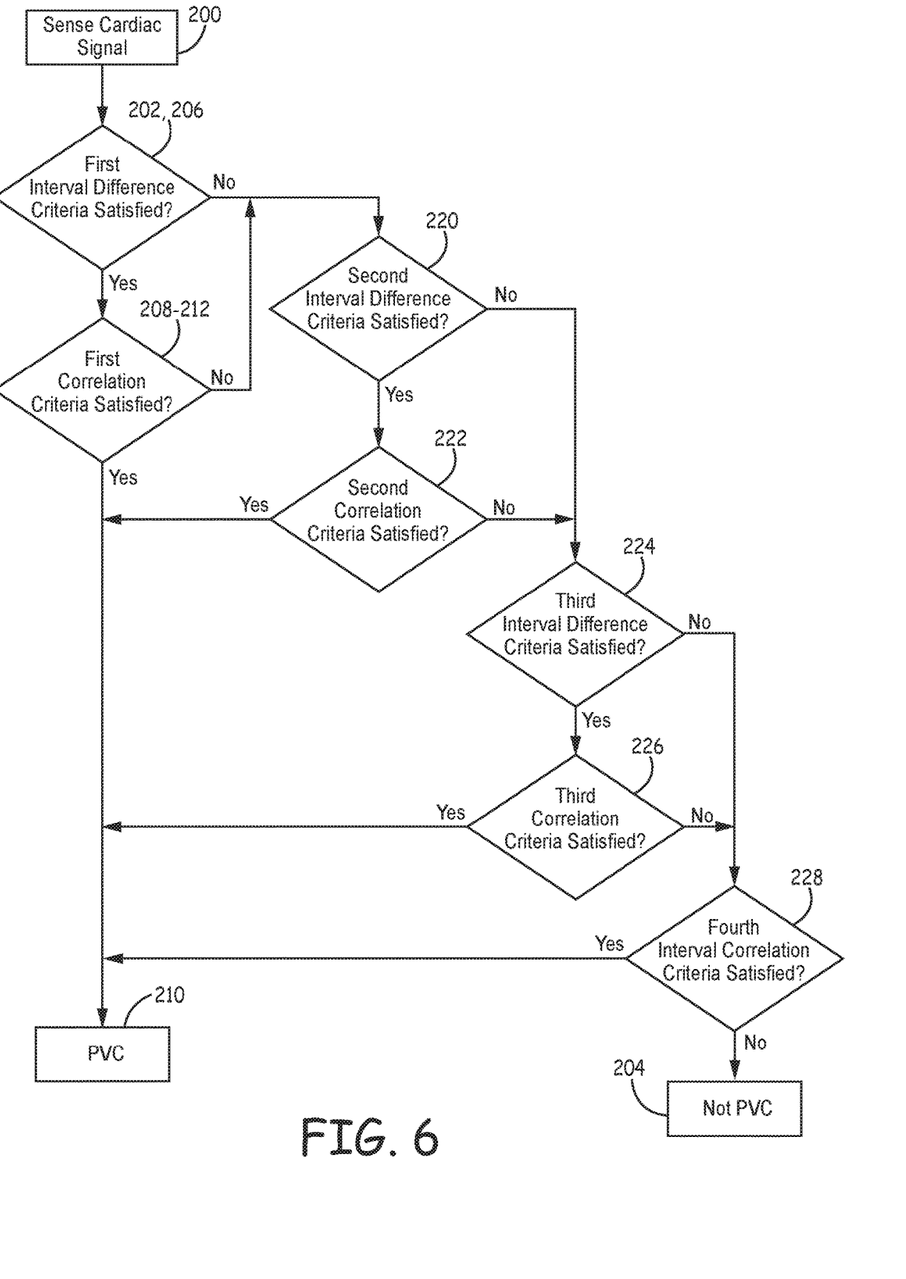
FIG. 6 is a flowchart of a method for detecting a premature ventricular contraction in a medical monitoring device according to an embodiment of the disclosure.

FIG. 6 is a flowchart of a method for detecting a premature ventricular contraction in a medical monitoring device according to an embodiment of the disclosure. According to an embodiment of the present disclosure, in order to improve sensitivity of the determination of the occurrence of a premature ventricular contraction, additional interval and correlation criteria may be utilized in addition to criteria 1 and criteria 2, described above. For example, as illustrated in FIG. 6, if either one of the first interval difference or the second interval difference is not satisfied (No in Block 202 or Block 206 of FIG. 5), additional interval criteria Block 220 and correlation criteria Block 222 may be utilized to determine the occurrence of a premature ventricular contraction. For example, according to one embodiment, the device may determine whether a ratio of the RR-interval associated with the second R-wave 106 and the RR-interval associated with first R-wave 104 ($RR_n/RR_{n-1}$) is less than an RR-interval ratio threshold, such as 1.25 for example, and whether a ratio of the RR-interval associated with the second R-wave 106 and the RR-interval associated with third R-wave 108 ($RR_n/RR_{n+1}$) is less than the RR-interval ratio threshold. In addition, a determination is made as to whether the RR-interval 212 associated with the second R-wave 106 ($RR_n$) is less than a secondary interval threshold, such as 800 ms for example. If both the RR-interval ratio threshold and the secondary interval threshold are satisfied, the additional interval criteria 220 is determined to be satisfied, Yes in Block 220, the device determines whether the secondary correlation threshold is satisfied, Block 222.

In this way, the device further determines the RR-interval criteria by evaluating the three RR-intervals 110-114 using the following secondary interval evaluation criteria:

Criteria 3: $RR_n/RR_{n-1} < 1.25$ and $RR_n/RR_{n+1} < 1.25$ and $RR_n < 800$ ms According to one embodiment, in order to determine whether the secondary correlation is satisfied, Block 222, the device determines whether one of two secondary correlation thresholds are satisfied. For example, a first secondary correlation is satisfied if a correlation ($C_{n-1,n+1}$) between the first R-wave 104 and the third R-wave 108 is greater than a first secondary correlation threshold, such 0.98, for example, and both a correlation ($C_{n-1,n}$) between the first R-wave 104 and the second R-wave 106 and a correlation ($C_{n,n+1}$) between the second R-wave 106 and the third R-wave 208 is less than a second secondary threshold, such as 0.75 for example. A second secondary correlation is satisfied if a correlation ($C_{n-1,n+1}$) between the first R-wave 104 and the third R-wave 108 is greater than a first secondary correlation threshold, such 0.95, for example, and both a correlation ($C_{n-1,n}$) between the first R-wave 104 and the second R-wave 106 and a correlation ($C_{n,n+1}$) between the second R-wave 106 and the third R-wave 208 is less than a second secondary threshold, such as 0.55 for example. In this way, the device further determines the RR-interval criteria by evaluating the three R-waves 104-108 using the following secondary correlation evaluation criteria:

Criteria 4: $\{C_{n-1,n+1} > 0.98$ and $C_{n-,n} < 0.75$ and $C_{n,n+1} < 0.75\}$ OR $\{C_{n-1,n+1} > 0.95$ and $C_{n-1,n} < 0.55$ and $C_{n,n+1} < 0.55\}$ If one of the first and the second secondary correlation criteria are satisfied, Yes in Block 222, and a premature ventricular contraction is determined to be identified, Block 210. If either the secondary interval criteria are not satisfied, No in Block 220, or if both the first and second secondary correlation criteria are not satisfied, No in Block 222, a premature ventricular contraction is not determined to occur, Block 204.

According to another embodiment, in order to further improve sensitivity the device may determine if third RR-interval and correlation criteria are satisfied. For example, if either the secondary interval criteria are not satisfied, No in Block 220, or if both the first and second secondary correlation criteria are not satisfied, No in Block 222, the device may determine additional interval criteria Block 224 and correlation criteria, Block 226, to determine the occurrence of a premature ventricular contraction. For example, according to one embodiment, the device may determine whether the RR-interval 112 associated with the second R-wave 106 ($RR_n$) is less than a first RR-interval threshold, such as 400 ms for example, and both the R-interval 110 associated with the first R-wave 104 ($RR_{n-1}$) and the RR-interval 114 associated with the third R-wave 108 ($RR_{n+1}$) are greater than a second interval threshold, such as 500 ms for example.

In this way, the device further determines the RR-interval criteria by evaluating the three RR-intervals 110-114 using the following third interval evaluation criteria:

Criteria 5: $RR_n < 400$ ms and $RR_{n-1} > 500$ ms and $RR_{n+1} > 500$ ms:

If the RR-interval 112 associated with the second R-wave is less than the first RR-interval threshold, and both the R-interval 110 associated with the first R-wave 104 and the RR-interval 114 associated with the third R-wave 108 are greater than a second interval threshold, the third interval criteria is determined to be satisfied, Yes in Block 224, and the device determines whether the third correlation criteria are met, Block 226.

According to an embodiment of the present disclosure, in order to determine whether the third correlation criteria are met, Block 226, the device determines whether a first correlation ($C_{n-1,n+1}$) between the first R-wave 104 and the third R-wave is greater than a third correlation threshold, such as 0.5 for example. In addition, the device determines whether a difference between the first correlation and a second correlation ($C_{n-1,n}$) determined between the first R-wave 104 and the second R-wave 106 is greater than a correlation threshold, such as 0.1 for example, and whether a difference between the first correlation and a third correlation ($C_{n,n+1}$) between the second R-wave 106 and the third R-wave is greater than the correlation difference threshold. In this way, the device further determines the RR-interval criteria by evaluating the three R-waves 104-108 using the following third correlation evaluation criteria:

Criteria 6: $C_{n-1,n+1} > 0.5$ and $C_{n-1,n+1} - C_{n-1,n} > 0.1$ and $C_{n-1,n+1} - C_{n,n+1} > 0.1$ If the first correlation between the first R-wave 104 and the third R-wave 108 is greater than the correlation threshold, and both the difference between the first correlation and the second correlation and the difference between the first correlation and the third correlation is greater than the correlation difference threshold, the third correlation threshold is determined to be satisfied, Yes in Block 226, and therefore a premature ventricular contraction is determined to occur, Block 210. On the other hand, if the first correlation between the first R-wave 104 and the third R-wave 108 is not greater than the correlation threshold, or either the difference between the first correlation and the second correlation or the difference between the first correlation and the third correlation is not greater than the correlation difference threshold, the third correlation threshold is not determined to be satisfied, No in Block 226, and therefore a premature ventricular contraction is not determined to occur, Block 204.

According to another embodiment, in order to further improve sensitivity the device may determine if fourth RR-interval criteria are satisfied. For example, if either the third interval criteria are not satisfied, No in Block 224, or if either one of the first and second third correlation criteria are not satisfied, No in Block 226, the device may determine additional interval criteria Block 228 to determine the occurrence of a premature ventricular contraction. For example, according to one embodiment, the device may determine whether a ratio of the RR-interval associated with the second R-wave 106 and the RR-interval associated with first R-wave 104 ($RR_n/RR_{n-1}$) is less than an RR-interval ratio threshold, such as 0.65 for example, and whether a ratio of the RR-interval associated with the second R-wave 106 and the RR-interval associated with third R-wave 108 ($RR_n/RR_{n+1}$) is less than then RR-interval ratio threshold. In addition, a determination is made as to whether the RR-interval 212 associated with the second R-wave 106 ($RR_n$) is less than a secondary interval threshold, such as 400 ms for example.

In this way, the device further determines the RR-interval criteria by evaluating the three RR-intervals 110-114 using the following fourth interval evaluation criteria:

Criteria 7: $RR_n/RR_{n-1}<0.65$ and $RR_n/RR_{n+1}<0.65$ and $RR_n<400$ ms

If both the RR-interval ratio threshold and the secondary interval threshold are satisfied, the fourth additional interval criteria is determined to be satisfied, Yes in Block 228, and the device determines that a premature ventricular contraction has occurred, Block 210. On the other hand, if either the RR-interval ratio threshold or the secondary interval threshold are not satisfied, the fourth additional interval criteria is determined not to be satisfied, no in Block 228, and the device determines that a premature ventricular contraction has not occurred, Block 204.

The method in principle can be extended to detect couplets (two consecutive premature ventricular intervals) or triplets (three consecutive ventricular intervals). In the case of a couplet, one would consider four RR intervals $RR_{n-2}$, $RR_{n-1}$, $RR_n$, and $RR_{n+1}$, with $RR_{n-1}$, $RR_n$, representing the couplet. All the RR interval criteria, namely criteria 1, 3, 5, 7, with $RR_{n-2}$, $RR_{n-1}$, replacing $RR_{n-1}$, $RR_n$, in the criteria and in the all the criteria where $RR_n$ is compared to an interval threshold will be replaced by comparing both $RR_{n-1}$, $RR_n$, to that same interval threshold. For example the modified criteria 7 could be Couplet criteria 7: $RR_{n-1}/RR_{n-2}<0.65$ and $RR_{n-1}/RR_{n+1}<0.65$ and $RR_n<400$ ms and $RR_{n-1}<400$ ms Similarly, for correlation thresholds, $C_{n-1,n}$ will be replaced by $C_{n-2,n-1}$ and $C_{n,n+1}$ will be replaced by $C_{n-1,n+1}$. Additionally, a new correlation criteria which compares the correlation between the couplet, $C_{n-1,n}$, will be compared to a correlation threshold and optionally added to criteria 2, 4, and 6. For example criteria 6 may be modified to Couplet criteria 6: $C_{n-2,n+1}>0.5$ and $C_{n-1,n}>0.5$ and $C_{n-2,n+1}-C_{n-2,n-1}>0.1$ and $C_{n-2,n+1}-C_{n-1,n+1}>0.1$ Once a premature ventricular contraction has been determined to occur, Block 210, the device may perform any one of or a number of tasks, such as storing the occurrence of premature ventricular contractions for future upload to an external device, storing the premature ventricular contractions and correlating the information with intermittent symptoms the patient may be experiencing to determine patient condition, using the information to provide a patient premature ventricular contraction burden diagnostic, such as the number that occur per day or per hour. The burden diagnostic may be utilized for risk stratification of the patient, such as for sudden cardiac death, for example, to identify patients who may be eligible for an EP study, which may then lead to a determination of the need for an implantable cardiac device, or to an ablation procedure being performed. In addition, the detection of the occurrence of premature ventricular contractions can be used as a computational device, such as for determining heart rate turbulence, or may be used to augment other detection algorithms, such as determining not to use such beats when determining respiration rate from ECG amplitude, or to reduce falsely detecting cardiac events, such atrial fibrillation, for example.

Thus, an apparatus and method have been presented in the foregoing description with reference to specific embodiments. It is appreciated that various modifications to the referenced embodiments may be made without departing from the scope of the invention as set forth in the following claims.

I claim:

1. A method of determining occurrence of a premature ventricular contraction in a medical device, comprising:
   sensing a cardiac signal and determining R-waves in response to the sensed cardiac signal;
   determining RR intervals between the determined R-waves;
   determining whether a first interval criteria is satisfied in response to the determined intervals;
   determining a correlation between the determined R-waves;
   determining whether a first correlation criteria is satisfied in response to the determined correlation, wherein determining whether a first correlation criteria is satisfied in response to the determined correlation comprises:
   determining a first R-wave of the determined R-waves, a second R-wave of the determined R-waves, and a third R-wave of the determined R-waves;
   determining a first correlation between the first R-wave and the third R-wave;
   determining whether the first correlation is greater than a first correlation threshold;
   determining a second correlation between the first R-wave and the second R-wave;
   determining whether a first difference between the first correlation and the second correlation is greater than a first correlation difference threshold;
   determining a third correlation between the second R-wave and the third R-wave;
   determining whether a second difference between the first correlation and the third correlation is greater than the first correlation difference threshold; and
   determining a premature ventricular contraction is occurring in response to the first correlation being greater than the first correlation threshold and both the first difference and the second difference being greater than the first correlation difference threshold.

2. The method of claim 1, wherein determining whether a first interval criteria is satisfied comprises:
   determining a first RR interval associated with a first R-wave of the determined R-waves, a second RR interval associated with a second R-wave of the determined R-waves, and a third RR interval associated with a third R-wave of the determined R-waves;

comparing the second RR interval with the first RR interval to generate a first interval difference;

determining whether the first interval difference is greater than an interval difference threshold;

comparing the second RR interval with the third RR interval to generate a second interval difference; and determining whether the second interval difference is greater than the interval difference threshold.

3. The method of claim 2, further comprising determining the premature ventricular contraction is not occurring in response to one of the first interval difference and the second interval difference not being greater than the interval difference threshold.

4. The method of claim 1, wherein determining whether a first correlation criteria is satisfied in response to the determined correlation comprises:

determining whether the first correlation is greater than a second correlation threshold;

determining whether the first difference between the first correlation and the second correlation is greater than a second correlation difference threshold;

determining whether the second difference between the first correlation and the third correlation is greater than the second correlation difference threshold; and determining a premature ventricular contraction is occurring in response to the first correlation being greater than the second correlation threshold and both the first difference and the second difference being greater than the second correlation difference threshold.

5. The method of claim 4, wherein determining whether a first correlation criteria is satisfied in response to the determined correlation comprises:

determining whether the first correlation is greater than a third correlation threshold;

determining whether the first difference between the first correlation and the second correlation is greater than a third correlation difference threshold;

determining whether the second difference between the first correlation and the third correlation is greater than the third correlation difference threshold; and determining a premature ventricular contraction is occurring in response to the first correlation being greater than the third correlation threshold and both the first difference and the second difference being greater than the third correlation difference threshold.

6. The method of claim 5, wherein the first correlation threshold is 0.9, the second correlation threshold is 0.8, the third correlation threshold is 0.7, the first correlation difference threshold is 0.1, the second correlation difference threshold is 0.3 and the third correlation difference threshold is 0.6.

7. A method of determining occurrence of a premature ventricular contraction in a medical device, comprising:

sensing a cardiac signal and determining R-waves in response to the sensed cardiac signal;

determining a first RR interval associated with a first R-wave of the determined R-waves, a second RR interval associated with a second R-wave of the determined R-waves, and a third RR interval associated with a third R-wave of the determined R-waves;

determining whether a first interval criteria is satisfied in response to the determined intervals;

determining a correlation between the determined R-waves;

determining whether a first correlation criteria is satisfied in response to the determined correlation;

determining, in response to one of the first interval criteria and the first correlation criteria not being satisfied, whether a ratio of the second RR interval and the first RR interval is less than an interval ratio threshold;

determining whether a ratio of the second RR interval and the third RR interval is less than the interval ratio threshold; and determining whether the second RR interval is less than an interval threshold.

8. A medical monitoring device for determining the occurrence of a premature ventricular contraction, comprising:

at least one sensing electrode for sensing a cardiac signal; and a processor configured to determine R-waves in response to the sensed cardiac signal, determine RR intervals between the determined R-waves, determine whether a first interval criteria is satisfied in response to the determined intervals, determine a correlation between the determined R-waves, determine whether a first correlation criteria is satisfied in response to the determined correlation, wherein the processor is configured to determine a first R-wave of the determined R-waves, a second R-wave of the determined R-waves, and a third R-wave of the determined R-waves, determine a first correlation between the first R-wave and the third R-wave, determine whether the first correlation is greater than a first correlation threshold, determine a second correlation between the first R-wave and the second R-wave, determine whether a first difference between the first correlation and the second correlation is greater than a first correlation difference threshold, determine a third correlation between the second R-wave and the third R-wave, determine whether a second difference between the first correlation and the third correlation is greater than the first correlation difference threshold, and determine a premature ventricular contraction is occurring in response to the first correlation being greater than the first correlation threshold and both the first difference and the second difference being greater than the first correlation difference threshold.

9. The medical monitoring device of claim 8, wherein the processor is configured to determine a first RR interval associated with a first R-wave of the determined R-waves, a second RR interval associated with a second R-wave of the determined R-waves, and a third RR interval associated with a third R-wave of the determined R-waves, compare the second RR interval with the first RR interval to generate a first interval difference, determine whether the first interval difference is greater than an interval difference threshold, compare the second RR interval with the third RR interval to generate a second interval difference, and determine whether the second interval difference is greater than the interval difference threshold.

10. The medical monitoring device of claim 9, wherein the processor is configured to determine the premature ventricular contraction is not occurring in response to one of the first interval difference and the second interval difference not being greater than the interval difference threshold.

11. The medical monitoring device of claim 8, wherein the processor is further configured to determine whether the first correlation is greater than a second correlation threshold, determine whether the first difference between the first correlation and the second correlation is greater than a second correlation difference threshold, determine whether the second difference between the first correlation and the third correlation is greater than the second correlation difference threshold, and determine a premature ventricular contraction is occurring in response to the first correlation being greater than the second correlation threshold and both the first difference and the second difference being greater than the second correlation difference threshold.

12. The medical monitoring device of claim 11, wherein the processor is configured to determine whether the first correlation is greater than a third correlation threshold, determine whether the first difference between the first correlation and the second correlation is greater than a third correlation difference threshold, determine whether the second difference between the first correlation and the third correlation is greater than the third correlation difference threshold, and determine a premature ventricular contraction is occurring in response to the first correlation being greater than the third correlation threshold and both the first difference and the second difference being greater than the third correlation difference threshold.

13. The medical monitoring device of claim 12, wherein the first correlation threshold is 0.9, the second correlation threshold is 0.8, the third correlation threshold is 0.7, the first correlation difference threshold is 0.1, the second correlation difference threshold is 0.3 and the third correlation difference threshold is 0.6.

14. The medical monitoring device of claim 8, wherein the medical monitoring device comprises a subcutaneous monitoring device.

15. The medical monitoring device of claim 8 wherein the at least one sensing electrode is a proximal electrode located at a proximal end of the medical monitoring device and a distal electrode located at a distal end of the medical monitoring device and wherein the medical monitoring device is an insertable cardiac monitoring device further comprising a housing having a length, a width and a depth, wherein the length is much greater than the width and the width is greater than the depth.

16. A method of determining occurrence of a premature ventricular contraction in a medical device, comprising:
sensing a cardiac signal and determining R-waves in response to the sensed cardiac signal;
determining RR intervals between the determined R-waves;
determining whether a first interval criteria is satisfied in response to the determined intervals;
determining a correlation between the determined R-waves;
determining whether a first correlation criteria is satisfied in response to the determined correlation;
determining, in response to one of the first interval criteria and the first correlation criteria not being satisfied, whether a second interval criteria is satisfied in response to the determined intervals;
determining, in response to the second interval criteria being satisfied, whether a second correlation criteria is satisfied in response to the determined correlation; and
determining the premature ventricular contraction is occurring in response to the second interval criteria and the second correlation criteria being satisfied.

17. The method of claim 16, wherein determining whether a second interval criteria is satisfied in response to the determined intervals comprises:
determining a first RR interval associated with a first R-wave of the determined R-waves, a second RR interval associated with a second R-wave of the determined R-waves, and a third RR interval associated with a third R-wave of the determined R-waves;
determining whether a ratio of the second RR interval and the first RR interval is greater than an interval ratio threshold;
determining whether a ratio of the second RR interval and the third RR interval is greater than the interval ratio threshold; and
determining whether the second RR interval is less than a first interval threshold.

18. The method of claim 17, wherein determining whether a second correlation criteria is satisfied in response to the determined correlation comprises:
determining a first R-wave of the determined R-waves, a second R-wave of the determined R-waves, and a third R-wave of the determined R-waves;
determining a first correlation between the first R-wave and the third R-wave;
determining whether the first correlation is greater than a first correlation threshold;
determining a second correlation between the first R-wave and the second R-wave;
determining whether the second correlation is less than a second correlation threshold;
determining a third correlation between the second R-wave and the third R-wave; and
determining whether the third correlation is less than the second correlation threshold.

19. The method of claim 18, further comprising:
determining whether a third interval criteria is satisfied in response to the determined intervals;
determining, in response to the third interval criteria being satisfied, whether a third correlation criteria is satisfied in response to the determined correlation; and
determining the premature ventricular contraction is occurring in response to the third interval criteria and the third correlation criteria being satisfied.

20. The method of claim 19, wherein determining whether a third interval criteria is satisfied in response to the determined intervals comprises:
determining whether the second RR interval is less than a second interval threshold;
determining whether the first RR interval is greater than a third interval threshold; and
determining whether the third RR interval is greater than the third interval threshold.

21. The method of claim 20, wherein determining whether a third correlation criteria is satisfied in response to the determined correlation comprises:
determining whether the first correlation is greater than a third correlation threshold;
determining whether a difference between the first correlation and the second correlation is greater than a difference threshold; and
determining whether a difference between the first correlation and the third correlation is greater than the difference threshold.

22. A medical monitoring device for determining the occurrence of a premature ventricular contraction, comprising:
at least one sensing electrode for sensing a cardiac signal; and
a processor configured to determine R-waves in response to the sensed cardiac signal, determine RR intervals between the determined R-waves, determine whether a first interval criteria is satisfied in response to the determined intervals, determine a correlation between the determined R-waves, determine whether a first correlation criteria is satisfied in response to the determined correlation, wherein the processor is configured to determine, in response to one of the first interval criteria and the first correlation criteria not being satisfied, whether a second interval criteria is satisfied in response to the determined intervals, determine, in response to the second interval criteria being satisfied, whether a second correlation criteria is satisfied in response to the determined correlation, and determine the premature ventricular contraction is occurring in response to the second interval criteria and the second correlation criteria being satisfied.

23. The medical monitoring device of claim 22 wherein the at least one sensing electrode is a proximal electrode located at a proximal end of the medical monitoring device and a distal electrode located at a distal end of the medical monitoring device and wherein the medical monitoring device is an insertable cardiac monitoring device further comprising a housing having a length, a width and a depth, wherein the length is much greater than the width and the width is greater than the depth.

24. The medical monitoring device of claim 22, wherein the processor is configured to determine a first RR interval associated with a first R-wave of the determined R-waves, a second RR interval associated with a second R-wave of the determined R-waves, and a third RR interval associated with a third R-wave of the determined R-waves, determine whether a ratio of the second RR interval and the first RR interval is greater than an interval ratio threshold, determine whether a ratio of the second RR interval and the third RR interval is greater than the interval ratio threshold, and determine whether the second RR interval is less than a first interval threshold.

25. The medical monitoring device of claim 24, wherein the processor is further configured to determine a first R-wave of the determined R-waves, a second R-wave of the determined R-waves, and a third R-wave of the determined R-waves, determine a first correlation between the first R-wave and the third R-wave, determine whether the first correlation is greater than a first correlation threshold, determine a second correlation between the first R-wave and the second R-wave, determine whether the second correlation is less than a second correlation threshold, determine a third correlation between the second R-wave and the third R-wave, and determine whether the third correlation is less than the second correlation threshold.

26. The medical monitoring device of claim 25, wherein the processor is configured to determine whether a third interval criteria is satisfied in response to the determined intervals, determine, in response to the third interval criteria being satisfied, whether a third correlation criteria is satisfied in response to the determined correlation, and determine the premature ventricular contraction is occurring in response to the third interval criteria and the third correlation criteria being satisfied.

27. The medical monitoring device of claim 26, wherein the processor is configured to determine whether the second RR interval is less than a second interval threshold, determine whether the first RR interval is greater than a third interval threshold, and determine whether the third RR interval is greater than the third interval threshold.

28. The medical monitoring device of claim 27, wherein the processor is configured to determine whether the first correlation is greater than a third correlation threshold, determine whether a difference between the first correlation and the second correlation is greater than a difference threshold, and determine whether a difference between the first correlation and the third correlation is greater than the difference threshold.

29. A medical monitoring device for determining the occurrence of a premature ventricular contraction, comprising:
at least one sensing electrode for sensing a cardiac signal; and
a processor configured to determine R-waves in response to the sensed cardiac signal, determine RR intervals between the determined R-waves, determine whether a first interval criteria is satisfied in response to the determined intervals, determine a correlation between the determined R-waves, determine whether a first correlation criteria is satisfied in response to the determined correlation, wherein the processor is configured to determine a first RR interval associated with a first R-wave of the determined R-waves, a second RR interval associated with a second R-wave of the determined R-waves, and a third RR interval associated with a third R-wave of the determined R-waves, determine, in response to one of the first interval criteria and the first correlation criteria not being satisfied, whether a ratio of the second RR interval and the first RR interval is less than an interval ratio threshold, determine whether a ratio of the second RR interval and the third RR interval is less than the interval ratio threshold, and determine whether the second RR interval is less than an interval threshold.

30. The medical monitoring device of claim 29 wherein the at least one sensing electrode is a proximal electrode located at a proximal end of the medical monitoring device and a distal electrode located at a distal end of the medical monitoring device and wherein the medical monitoring device is an insertable cardiac monitoring device further comprising a housing having a length, a width and a depth, wherein the length is much greater than the width and the width is greater than the depth.

31. A non-transitory, computer-readable storage medium storing instructions for causing a processor included in a medical monitoring device to perform a method for determining occurrence of a premature ventricular contraction, the method comprising:
sensing a cardiac signal and determining R-waves in response to the sensed cardiac signal;
determining RR intervals between the determined R-waves;
determining whether a first interval criteria is satisfied in response to the determined intervals;
determining a correlation between the determined R-waves;
determining whether a first correlation criteria is satisfied in response to the determined correlation, wherein determining whether a first correlation criteria is satisfied in response to the determined correlation comprises:
determining a first R-wave of the determined R-waves, a second R-wave of the determined R-waves, and a third R-wave of the determined R-waves;
determining a first correlation between the first R-wave and the third R-wave:
determining whether the first correlation is greater than a first correlation threshold;
determining a second correlation between the first R-wave and the second R-wave;
determining whether a first difference between the first correlation and the second correlation is greater than a first correlation difference threshold;
determining a third correlation between the second R-wave and the third R-wave;

determining whether a second difference between the first correlation and the third correlation is greater than the first correlation difference threshold; and determining a premature ventricular contraction is occurring in response to the first correlation being greater than the first correlation threshold and both the first difference and the second difference being greater than the first correlation difference threshold.

\* \* \* \* \*